United States Patent [19]

Kochavi et al.

[11] Patent Number: 5,156,773
[45] Date of Patent: Oct. 20, 1992

[54] STABILIZED ENZYMATIC LIQUID DETERGENT COMPOSITION

[75] Inventors: Daniel Kochavi, Fairfield; Vicki Lentner, Danbury, both of Conn.

[73] Assignee: Novo Nordisk A/S, Bagsvaerd, Denmark

[21] Appl. No.: 448,973

[22] Filed: Dec. 12, 1989

[51] Int. Cl.$^5$ .......................... C11D 1/90; C11D 7/42; C12N 9/00
[52] U.S. Cl. .................... 252/547; 252/546; 252/174.12; 252/DIG. 12; 435/188
[58] Field of Search .................. 252/174.12, 546, 547, 252/DIG. 12; 435/188

[56] References Cited

U.S. PATENT DOCUMENTS

| | | | |
|---|---|---|---|
| 3,557,002 | 1/1971 | McCarty | 252/174.12 |
| 3,634,266 | 1/1972 | Theile et al. | 252/132 |
| 3,707,505 | 12/1972 | Maeda et al. | 252/136 |
| 3,819,528 | 6/1974 | Berry | 242/153 |
| 3,840,840 | 10/1974 | Barrat et al. | 252/545 |
| 4,543,333 | 9/1985 | Eilertsen et al. | 435/188 |
| 4,670,179 | 6/1987 | Inamorato et al. | 252/174 |

FOREIGN PATENT DOCUMENTS

| | | |
|---|---|---|
| 26284 | 3/1976 | Japan. |
| 58-021498 | 2/1983 | Japan. |
| 1108387 | 5/1986 | Japan. |
| 123600 | 7/1987 | Japan. |
| 1283213 | 11/1989 | Japan. |

*Primary Examiner*—A. Lionel Clingman
*Assistant Examiner*—Kery A. Fries
*Attorney, Agent, or Firm*—Fidelman & Wolffe

[57] ABSTRACT

Stabilized enzymatic liquid detergent composition, stabilized by containing therein 0,1–10%, most preferably 0.25–5% of a compound having the following formula:

$$R-\underset{\underset{CH_3}{|}}{\overset{\overset{CH_3}{|}}{N}}-(CH_2)_n-COO^- \qquad (I)$$

R is zero, or $C_1$-12 alkyl, or $C_{11}$-17alkyl—CONH—$(CH_2)_3$ n is 1–3.

12 Claims, No Drawings

STABILIZED ENZYMATIC LIQUID DETERGENT COMPOSITION

TECHNICAL FIELD

This invention concerns stabilized enzymatic liquid detergent compositions for cleaning a wide range of items including hard surfaces and soft goods such as textiles both for commercial and home use.

BACKGROUND ART

Aqueous liquid enzymatic detergents are well-known in the prior art. The enzymes incorporated in liquid detergents have mostly been Bacillus protease, but the prior art also suggests that incorporation of enzymes other than Bacillus proteases may be useful, e.g., other enzyme types (such as amylases, lipases and cellulase) as well as enzymes of non-Bacillus origin (e.g., fungal enzymes). A major problem which is encountered with such compositions is that of ensuring a sufficient storage stability of the enzymes in such compositions.

The prior art deals extensively with stabilization of enzymes in liquid detergents. It is known that a number of commonly used detergent ingredients may reduce their storage stability, e.g., aniomic surfactants and detergent builders. The prior art also suggest that various materials that are not detergent-active can be incorporated as enzyme stabilizers.

It can also be mentioned that JP-A 58-194,806 and JP-A 58-069,808 suggest the incorporation of imidazoline amphoteric surfactant in tooth paste to improve the storage stability of amylase; this teaching has apparently not been utilized in detergents.

It is now the object of the invention to provide a liquid detergent composition comprising a detergent enzyme with improved storage stability.

STATEMENT OF THE INVENTION

The object of the invention is achieved by providing a stabilized enzymatic liquid detergent composition comprising (a) an effective amount of a microbial enzyme
(b) from about 0.1 to 10% by weight of an amphoteric compounds having the general formula (I)

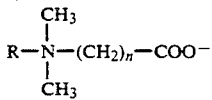

(I)

R is zero, or $C_{1-12}$ alkyl, or $C_{11-17}$ alkyl $-CONH-(CH_2)_3$ n is 1-3

In preferred compounds of formula (I) R is zero or $CH_3$, n is 1, i.e., dimethylglycine, and betaine.

In the propyl amido compounds of formula (I), the alkanoyl moiety is a saturated, unbranched and unsubstituted $C_{12-18}$ Preferred examples of the group R are those derived from coco acids (mainly $C_{12}-C_{14}$) and from tallow acids (mainly $C_{16}-C_{18}$), e.g., lauryl, stearyl, palmityl.

Preferred proportions for the stabilizer compound are in the range of 0.25-10%, more preferably, 0.5-5% by wt of the liquid detergent composition.

DETAILED DESCRIPTION OF THE INVENTION

Microbial Enzyme

Microbial enzymes suitable for the present compositions include proteases, lipases, amylases and cellulases. The enzymes are derived from microbial sources, such as Bacillus and fungi. Some specific examples of detergent enzymes follow, each identified by enzyme type, microbial source and reference to a commercial product and/or a patent publication:

Protease of *Bacillus*, especially from *B. licheniformis* (e.g. Alcalase TM) and from alkalophilic Bacillus strains according to U.S. Pat. No. 3,723,250 (e.g. Savinase TM) (all available from Novo-Nordisk A/S)

Alpha-amylase of *Bacillus*, especially *B. licheniformis*. Termamyl TM (Novo Industri A/S)

Protease of Fusarium, especially *f. oxysporum*, U.S. Pat. No. 3,652,399 (Takeda)

Protease according to DK 6376/87 (Novo)

Cellulase of *Humicola*, especially *H. insolens*. Celluzyme TM (Novo Industry A/S), U.S. Pat. No. 4,435,307 (Novo)

Lipase of *Humicols*, especially *H. lanuginosa*. Lipolase TM (Novo), EP 177,183 (Novo).

The detergent of the invention may contain two or more detergent enzymes. Examples are combinations of any two of the above enzymes, especially combinations of a Bacillus protease and any one of the above enzymes.

Amphoteric Compound of Formula (I)

Commercially available example of amphoteric compounds having the general formula (I) includes betaine. A related compound is dimethyl glycine; both are preferred compounds. The respective formulae of the two are as follows:

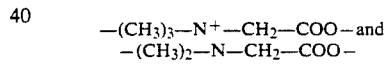

Surfactants

The detergent composition of the invention will usually also contain a nonionic surfactant, e.g., about 3-20% by weight. Further, the composition may optionally contain anionic surfactant and/or a second amphoteric surfactant, e.g., about 3-15% by weight.

Examples of suitable surfactants are:

Nonionics: Nonyl phenol ethoxylate, alcohol ethoxylate.

Anionics: linear alkylbenzene sulfonate, secondary alkane sulfonate, alcohol ethoxylate sulfate, alpha olefin sulfonate.

Other Ingredients

The liquid detergent of the invention may be aqueous, e.g., containing 20-70% of water and 0-20% of solvent, e.g., ethanol, propyleneglycol, or containing 1-20% of water and 5-25% of solvent. Satisfactory enzyme stability may be obtained even at water contents above 50%. Alternatively, it may be essentially free of water (e.g., water content below 1%), and will then typically contain 10-30% of solvent.

Typical solvents are mono- and dihydroxy lower alcohols and glycol ethers.

The detergent composition of the invention may be built (i.e., comprising a detergent builder) or unbuilt (i.e., essentially free of a detergent builder).

A soluble calcium salt may be included suitably in the range of about 1-20 millimole/l since calcium ion stabilizes many detergent enzymes.

pH will typically be neutral or alkaline, particularly preferred between 8-10.

The compositions may also contain, depending on the intended use, one or more of the usual known in the art detergent additives such as fabric conditioner (e.g., quaternary ammonium salts, typically 1-5%), foam boosters (e.g., 1-5%), bactericides (e.g., 1-5%), optical brighteners (e.g., 0.1-1%), dyes (e.g., 0.1-1%) and perfumes (e.g., 0.1-1%). Such additives are commonly present in detergent formulations.

In the following Examples the samples were stored at 37° C., the enzyme activity was measured before and after storage, and the results were expressed as residual activity in % of initial activity.

Example I

Detergent base I composition, w/w
- Nonionic (Neodol 25-7) AE: 25%
- Anionic (Neodol 25-35) AES: 5%
- Triethanolamine: 5%
- Ethanol: 10%
- Stabilizer (see table below): 5% (control - no stabilizer)
- protease: 1%
- amylase: 0.3%
- water: up to 100%

Final pH = 9.0

Stability at 37° C. with various stabilizer

| Stabilizer | % Protease Activity Left After 8 Weeks | | | % Amylase Activity Left After Six Weeks Termamyl | | |
|---|---|---|---|---|---|---|
| | Alcalase | Esperase | Savinase | + Alcalase | + Esperase | + Savinase |
| none | 48 | 58 | 48 | 86 | 98 | 94 |
| Bentaine | 65 | 78 | 70 | 86 | 86 | 84 |
| Dimethyl glycine | 74 | 79 | 66 | 110 | 72 | 91 |
| Alkyl amino Propyl betaine | | | | | | |
| Cocoyl | 67 | 74 | 61 | 95 | 77 | 91 |
| Isostearyl | 65 | 76 | 60 | 62 | 74 | 118 |
| Myristoyl | 68 | 65 | 59 | 41 (?) | 97 | 93 |
| Palmytoyl | 57 | 65 | 61 | 62 | 84 | 107 |

Example II

Detergent base II
- Nonionic (Neodol 25-7) AE: 25%
- Anionic (Vista C-550) LAS: 5%
- Triethanolamine: 5%
- Ethanol: 10%
- Stabilizer: 0 (control), 0.5, 2.5, 5%
- protease: 1%
- amylase: 0.3%
- water: up to 100%
- adjust to pH = 90

Stability at 37° C. with various stabilizer

| Stabilizer | | % Activity left after 8 weeks | | |
|---|---|---|---|---|
| | | Alcalase | Savinase | Termamyl |
| none | | 43 | 38 | 69 |
| Bentaine, | 0.5 | 56 | 52 | 74 |
| | 2.5 | 59 | 53 | 74 |
| | 5.0 | 66 | 53 | 74 |
| Dimethylglycine, | 0.5 | 63 | 53 | 76 |
| | 2.5 | 65 | 53 | 76 |
| | 5.0 | 66 | 56 | 74 |

We claim:

1. A stabilized enzymatic aqueous liquid detergent composition containing about 3-35% by wt of surfactant therein which also comprises
   (a) a cleaning effective amount of at least one microbial enzyme and
   (b) from about 1 to 10% by weight of a stabilizer compound having the general formula (I)

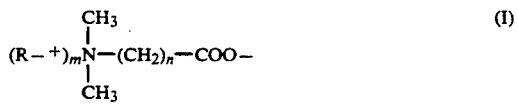

wherein m is 0 or 1, R is [$C_{1-12}$ alkyl, or $C_{11-17}$ alkyl - CONH - $(CH_2)_3$]methyl, n is 1-3.

2. A detergent composition according to claim 1, wherein said stabilizer has the formula:

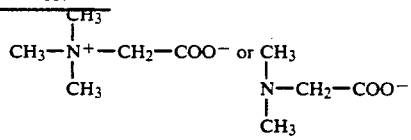

3. A detergent composition according to claim 1 wherein the enzyme is a Bacillus protease, amylase or cellulase.

4. A detergent composition according to claim 1, wherein the enzyme is a fungal detergent protease, a lipase, or a cellulase.

5. A detergent composition according to claim 4, wherein the enzyme is a Fusarium protease, a Humicola lipase or a Humicola cellulase.

6. A detergent composition according to claim 1, further containing a cleaning effective amount of two microbial enzymes.

7. A detergent composition according to claim 1, containing from about 0.5 to 5% by weight of said stabilizer compound.

8. A detergent composition according to claim 1, including from about 1 to 20% by weight of a nonionic surfactant.

9. A detergent composition according to claim 1, further containing from about 20 to 70% by weight of water and from up to about 20% by weight of a solvent.

10. A detergent composition according to claim 1, containing from about 1 to 40% by weight of a detergent builder.

11. A detergent composition according to claims containing a soluble calcium salt in an amount giving from about 1 to 20 millimoles of calcium per liter.

12. A stabilized enzymatic liquid detergent composition containing about 3-35% wt of surfactant therein which also comprises (a) a cleaning effective amount of at least one microbial enzyme and
(b) from about 1 to 10% by weight of a stabilizer compound having the general formula (I)

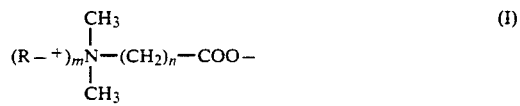

wherein m is O or 1, R is [$C_{1-12}$ alkyl, or $C_{11-17}$ alkyl - CONH - $(CH_2)3$]methyl, n is 1-3,
said composition being essentially free of water and which contains from about 10 to 30% of a solvent.

* * * * *